(12) United States Patent
Rehkemper

(10) Patent No.: US 7,310,844 B1
(45) Date of Patent: Dec. 25, 2007

(54) TOOTHBRUSH WITH MANUAL POWERED MOVABLE BRUSH HEAD

(75) Inventor: Steven Rehkemper, Chicago, IL (US)

(73) Assignee: REHCO LLC, Chicago, IL (US)

( * ) Notice: Subject to any disclaimer, the term of this patent is extended or adjusted under 35 U.S.C. 154(b) by 222 days.

(21) Appl. No.: 11/179,398

(22) Filed: Jul. 13, 2005

(51) Int. Cl.
*A61C 17/22* (2006.01)
*F03G 1/00* (2006.01)

(52) U.S. Cl. .............................. 15/22.1; 15/28; 185/37; 185/39

(58) Field of Classification Search ................. 15/22.1, 15/22.2, 22.3, 22.4, 23, 25, 26, 28; 185/37, 185/39
See application file for complete search history.

(56) References Cited

U.S. PATENT DOCUMENTS

| | | | | |
|---|---|---|---|---|
| 931,143 | A * | 8/1909 | Phillips | 15/23 |
| 1,283,599 | A * | 11/1918 | Thomas | 185/37 |
| 1,947,324 | A * | 2/1934 | Zerbee | 15/28 |
| 1,961,243 | A * | 6/1934 | Pereira | 185/37 |
| 2,189,408 | A * | 2/1940 | Seifried | 15/28 |
| 2,249,441 | A * | 7/1941 | Sussman | 185/39 |
| 2,259,964 | A * | 10/1941 | Sussman | 15/23 |
| 2,261,059 | A * | 10/1941 | Gris | 15/23 |
| 2,682,066 | A * | 6/1954 | Keely | 15/22.1 |
| 3,115,652 | A * | 12/1963 | Zerbee | 15/28 |
| 3,138,813 | A * | 6/1964 | Kaplan | 15/22.1 |
| 3,241,169 | A * | 3/1966 | Windward | 15/22.1 |
| 3,284,829 | A * | 11/1966 | Allen | 15/22.1 |
| 3,623,175 | A * | 11/1971 | Emerson | 15/142 |
| 6,000,083 | A * | 12/1999 | Blaustein et al. | 15/28 |
| 6,421,865 | B1 * | 7/2002 | McDougall | 15/22.1 |

FOREIGN PATENT DOCUMENTS

| | | | |
|---|---|---|---|
| DE | 2411041 | * | 9/1975 |
| DE | 4313970 | * | 11/1994 |
| DE | 2004003485 U1 | * | 7/2004 |
| GB | 2383262 | * | 6/2003 |
| WO | 03/000090 | * | 1/2003 |

* cited by examiner

*Primary Examiner*—Mark Spisich
(74) *Attorney, Agent, or Firm*—Adam K. Sacharoff; Much Shelist

(57) ABSTRACT

This application includes a number of embodiments of a spring powered toothbrush for cleaning teeth. A wind-up spring is located in the base of the toothbrush which spring provides power for a gear train including a drive shaft assembly that is designed to bring about rapid movement of the brush portion of the toothbrush to aid in cleaning the teeth. The drive mechanism is controlled by a spring biased push button in the toothbrush housing. In one version the brush portion of the toothbrush includes a rotatable brush section that is gear driven by the drive shaft. In another version the upper portion of the toothbrush is vibrated by an offset weight connected to the drive shaft and in a third version the drive shaft includes an offset weight that acts to oscillate a movable brush section by intermittent engagement between the; weight and brush section.

7 Claims, 7 Drawing Sheets

US 7,310,844 B1

TOOTHBRUSH WITH MANUAL POWERED MOVABLE BRUSH HEAD

BACKGROUND OF THE INVENTION

The oral care market has, in recent years, been literally flooded with various kinds of power-driven toothbrushes. These have included electrically operated brushes, pump-driven brushes and those with relatively complex mechanical arrangements to rotate, oscillate and vibrate the brush portions to accomplish a more pro-active cleaning of the teeth and removing particles between the teeth.

There has long been a need for an inexpensive, effective, easy to handle, fully portable oral cleaning device that has a long life, is simple to operate and does not have to rely on electric power, water pressure or a series of complex mechanisms that tend to fail.

SUMMARY OF THE INVENTION

In accordance with the invention there is provided three embodiments of toothbrushes with movable bristles that are powered by a simple wind-up mechanical system that is very simple to operate. The components basically consist of a spring that is wound to provide a spring force that loads a mechanism to provide power to move the bristles of a toothbrush. The drive mechanism essentially consists of an end cap assembly containing a spring that is wound by a crank arm to load a drive shaft through a series of gears which shaft creates various movements of the bristles depending on the connection of the drive shaft with the bristles. The force is stored in the spring and gear assembly by a clutch mechanism that is controlled by a push button in the handle portion of the brush. When the button is pushed the stored up spring force moves the brush bristles until the spring force is expended. To repeat the bristle movement the spring is rewound and the action will be repeated.

In one embodiment the drive shaft drives a crown gear connected to a gear portion on the bristle section that forms a brush head to provide a rotating action to the brush head.

In a second embodiment the drive shaft has connected to its end adjacent the brush head an offset weight which when rotated vibrates the brush head to obtain the desired rapid movement of the brush to obtain the desired brushing effect.

In a third embodiment the brush head includes a spring-biased lever member that is engaged by an offset weight/cam, which offset member repeatedly engages the lever to oscillate the brush head. Essentially, the brush head lever is engaged by the weight to move the brush head in one direction and after engaging and releasing the brush head the spring returns the lever and brush head to its initial position and the weight again engages the lever to bring about the rapid oscillating action until the spring force is dissipated.

BRIEF DESCRIPTION OF THE DRAWINGS

The invention will be more fully understood from the drawings and the full description thereof in which.

DETAILED DESCRIPTION OF THE DRAWINGS

Figure 1:
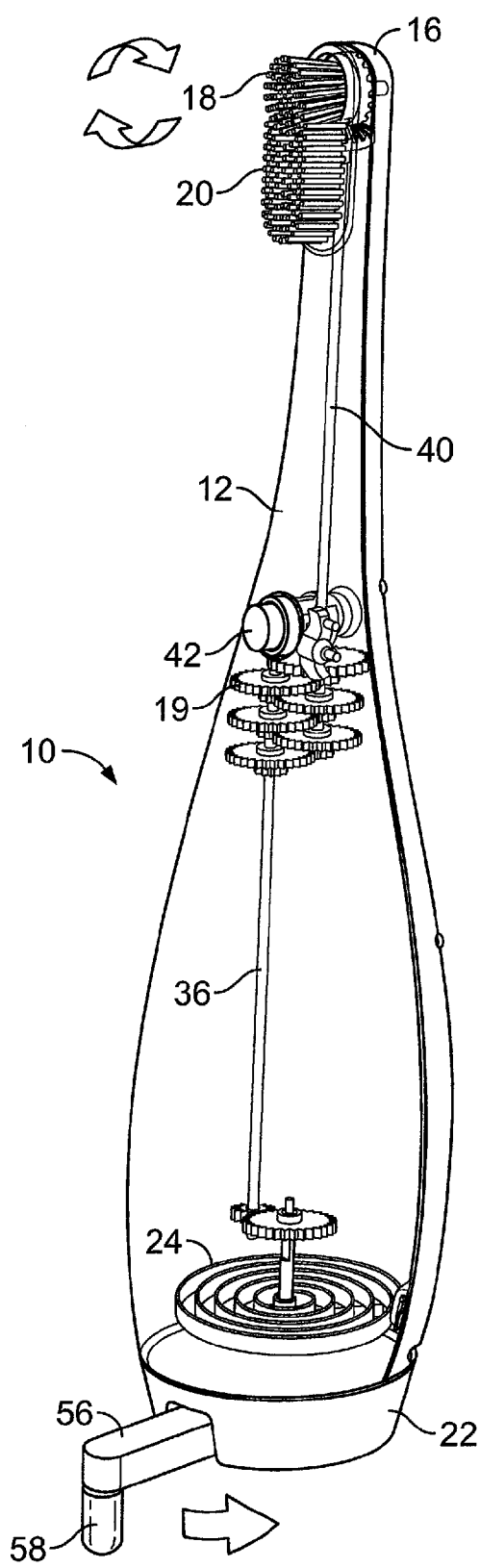
FIG. 1 is a perspective view showing the internal components of applicant's novel wind-up spring-powered toothbrush in which the brush head is power driven through a gear mechanism.
Figure 2:
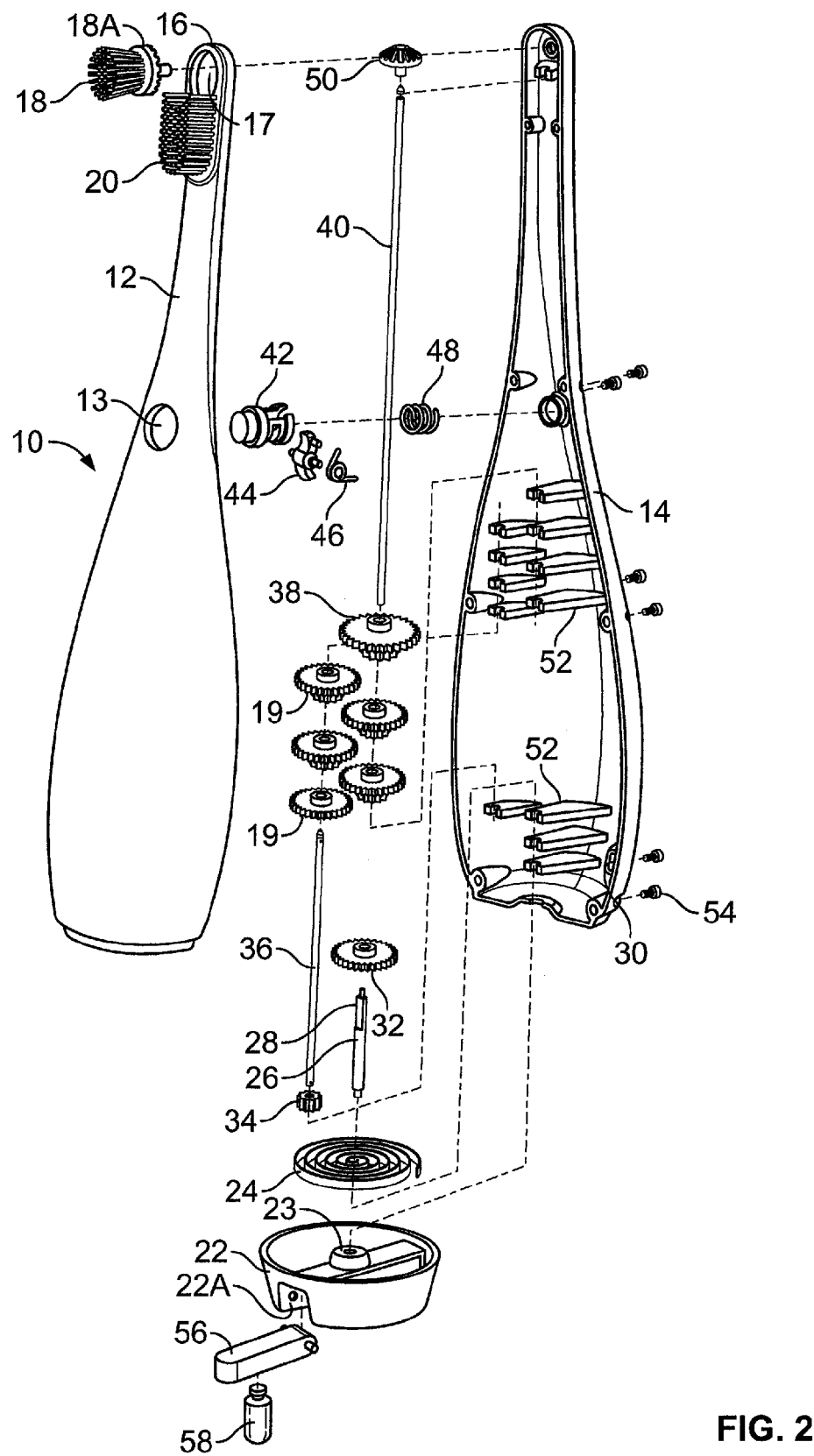
FIG. 2 is an exploded perspective view of the toothbrush of FIG. 1.

While there are three embodiments, the underlying spring power source for each of the three embodiments is identical and will only be described with respect to the embodiment shown in FIGS. 1 and 2.

Referring to FIG. 1 there is illustrated, in perspective, a toothbrush including a generally cylindrical brush head portion that is rotated by a spring powered gear system.

Specifically, there is illustrated a toothbrush housing 10 made up of a front brush housing portion 12 that includes a button opening 13, the purpose of which will be discussed hereinafter, and a rear brush housing portion 14. Located in the upper portion 16 of the front brush housing 12 is an opening 17 that rotatably retains the generally cylindrical brush head 18. On the back of the brush head 18 is a gear 18A that is engaged by the spring driven gear assembly 19 to rotate the brush head 18. The brush head 18 lies adjacent a fixed brush portion 20. It can be appreciated that brush head 18 and fixed brush portion 20 form the typical brushing area of a toothbrush and will function as a normal toothbrush when desired.

FIG. 2 is an exploded view of the toothbrush of FIG. 1. The power drive mechanism for regulating the movement of the brush head or the total brush portion is identical for all three embodiments and thus the same numbers will be used with respect thereto. The differences reside in the interrelationship between the drive shaft and the movable brush head and the total brush portion of the toothbrush.

In FIGS. 1 and 2 there is illustrated the embodiment of the wind-up spring-powered toothbrush in which the brush head 18 is rotated by the drive shaft 40 through the interconnection between a crown gear 50 on the end of the drive shaft 40 and the gear 18A on the back of the brush head 18.

The power source for the drive shaft 40 is generated by the rotation of the cap 22 connected to a wind-up spring 24 by a lever 56 pivotally connected to the cap and operated by a handle 58. The cap 22 defines a recess 22A into which the lever 56 fits.

The wind-up spring 24 has its outer end in the spring end receiving member 30 connected to the rear brush housing 14. The inner end of the spring 24 is secured to the spring axle 26 by being disposed in the slot 28 of the axle 26. The bottom end of the axle 26 fits into the opening 23 of the cap 22 and thus the spring 24 is wound-up by the rotation of the cap 22.

The gear drive to speed up the rotation of the drive shaft consists of the axle driven gear 32 connected to the drive axle 26, pinion gear 34, gear axle 36 and gears 19. The operation of the spring driven axle and various gears to rotate the drive shaft 40 at a high speed is controlled by a clutch gear 38.

The operation of the clutch gear 38 by a push button assembly comprises a push button 42 that is resiliently biased outwardly in the opening 13 of the front brush housing portion 12 for operating access by the operator of the toothbrush. The outward biasing of the push button 42 is effected by the brush button return spring 48. The inward movement of the push button 42 acts against the clutch pin 44 which clutch pin is normally biased into engagement with the clutch gear 38 to prevent the clutch gear from rotating. When the push button 42 acts against the clutch pin 44 and return spring 48, the clutch is released and the stored-up energy in the spring-loaded gear drive rotates the drive shaft 40 at a high speed. This high speed rotation of the drive shaft rapidly rotates the brush head 18 by the inter-engagement of the crown gear 50 on the drive shaft 40 and the gear 18A on the back of the brush head.

It remains to note that the rear housing 14 of the toothbrush includes suitable supports for the various shafts to retain them in proper alignment when the front and rear housings 12, 14 are fastened together by the screws 54.

Figure 3:
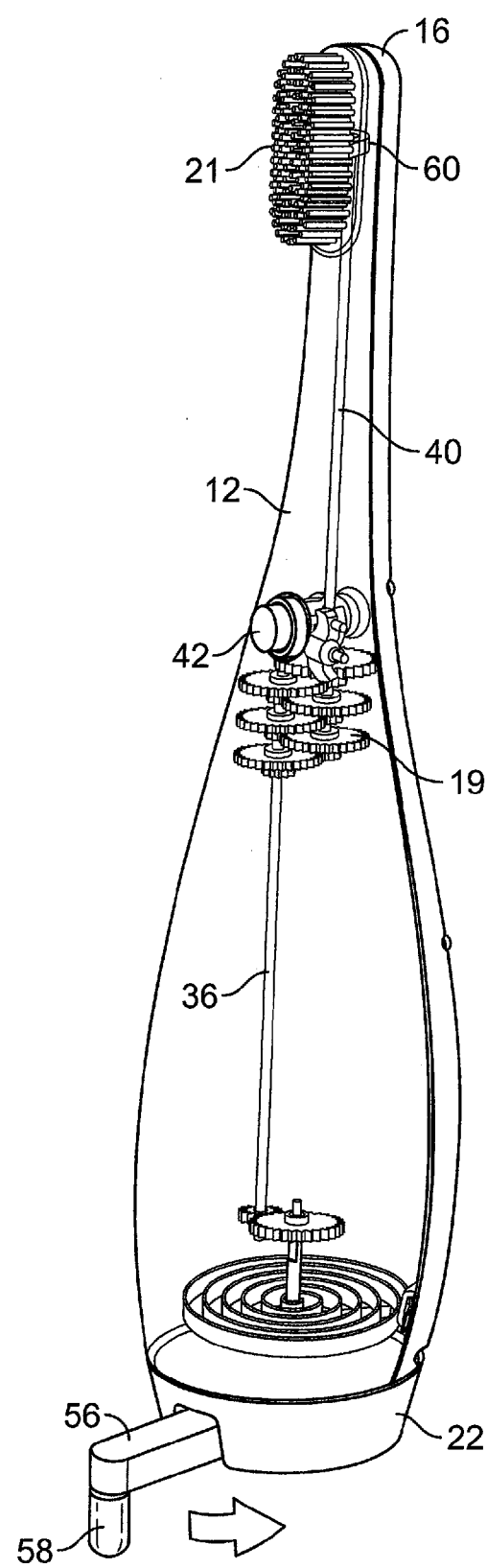
FIG. 3 is a perspective view of a second embodiment similar to FIG. 1 in which the brush portion of the toothbrush is vibrated by a power driven offset weight located adjacent the brush portion.
Figure 4:
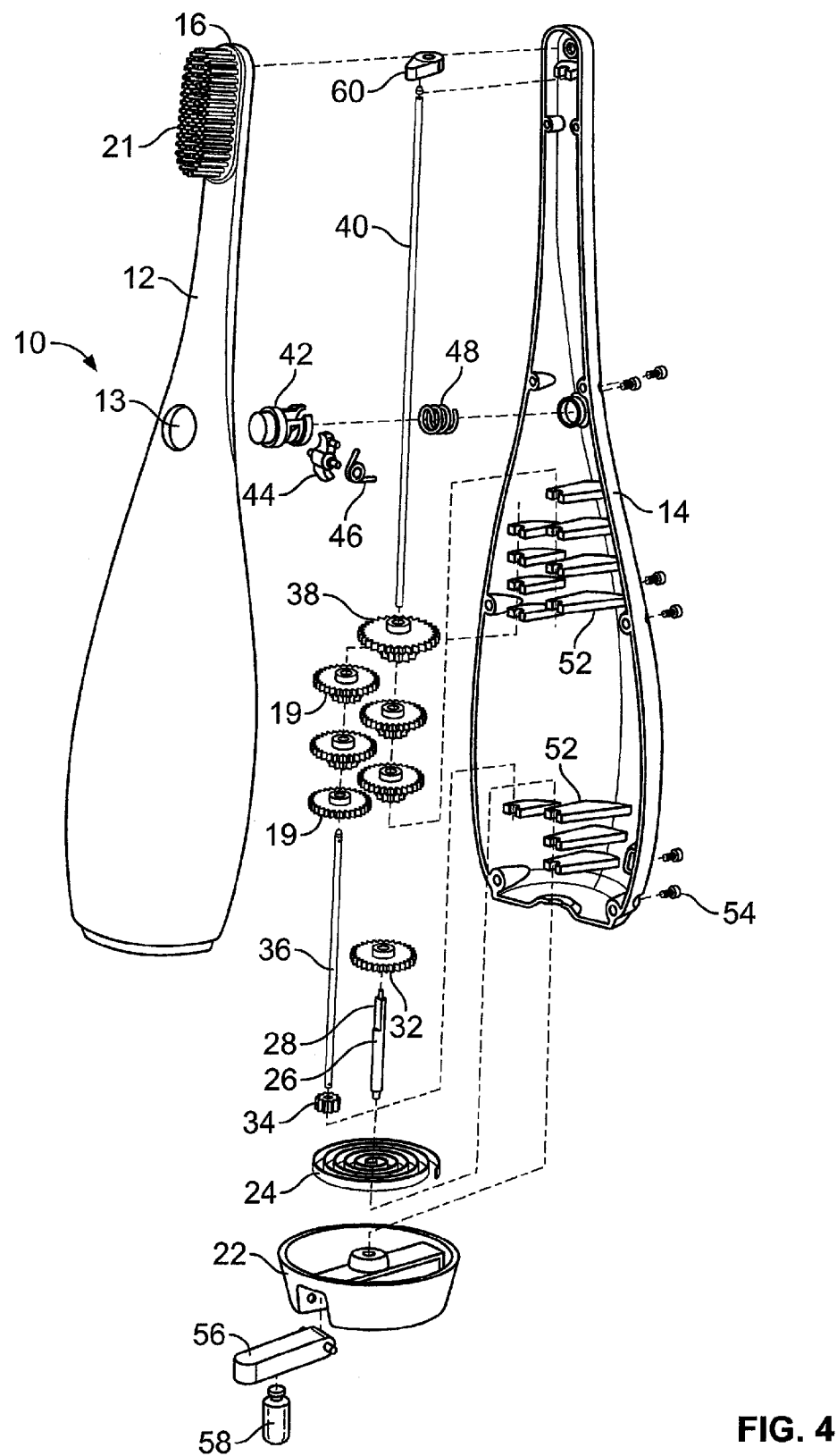
FIG. 4 is an exploded perspective view of the toothbrush of FIG. 3.

Turning now to the second embodiment of the spring-powered toothbrush illustrated in FIGS. 3 and 4, it is noted that the spring-powered arrangement for the drive shaft 40 is identical to that illustrated in the embodiment illustrated in FIGS. 1 and 2. Thus the identical numbers for the various identical parts have been used and the operation thereof has been described in detail with respect to FIGS. 1 and 2.

The second embodiment differs from the first in that the brush portion is a single elongated series of brush segments 21 that fit into the upper portion 16 of the front brush housing 12. There is no rotatable brush head like that shown in the first embodiment of FIGS. 1 and 2.

The difference between the first and second embodiments is that in place of the rotatably driven brush head of FIG. 2, the entire brush section 21 is vibrated by a power rotated offset weight 60 located in the upper portion of the toothbrush adjacent the brush section 21.

Referring specifically to FIG. 4, at the upper end of the drive shaft 40 there is located the offset weight 60. Thus, after the spring 24 is wound and the button 42 pushed in to release the clutch gear 38, the drive shaft 40 and weight 60 is rapidly rotated to vibrate the upper portion of the toothbrush housing and the brush section 21. This action results in the brush action generally comparable to that obtained by the gear arrangement of FIGS. 1 and 2.

Figure 5:
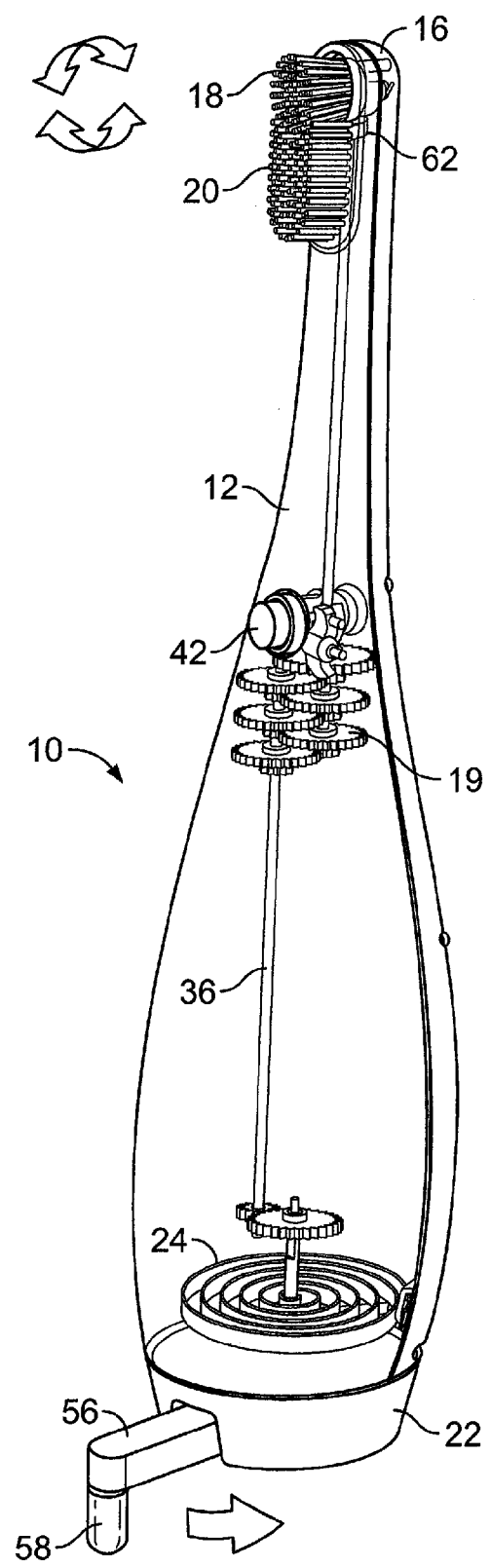
FIG. 5 is a perspective view of a third embodiment similar to FIG. 1 in which the brush head portion is oscillated by an offset weight and an associated spring-biased lever assembly.
Figure 6:
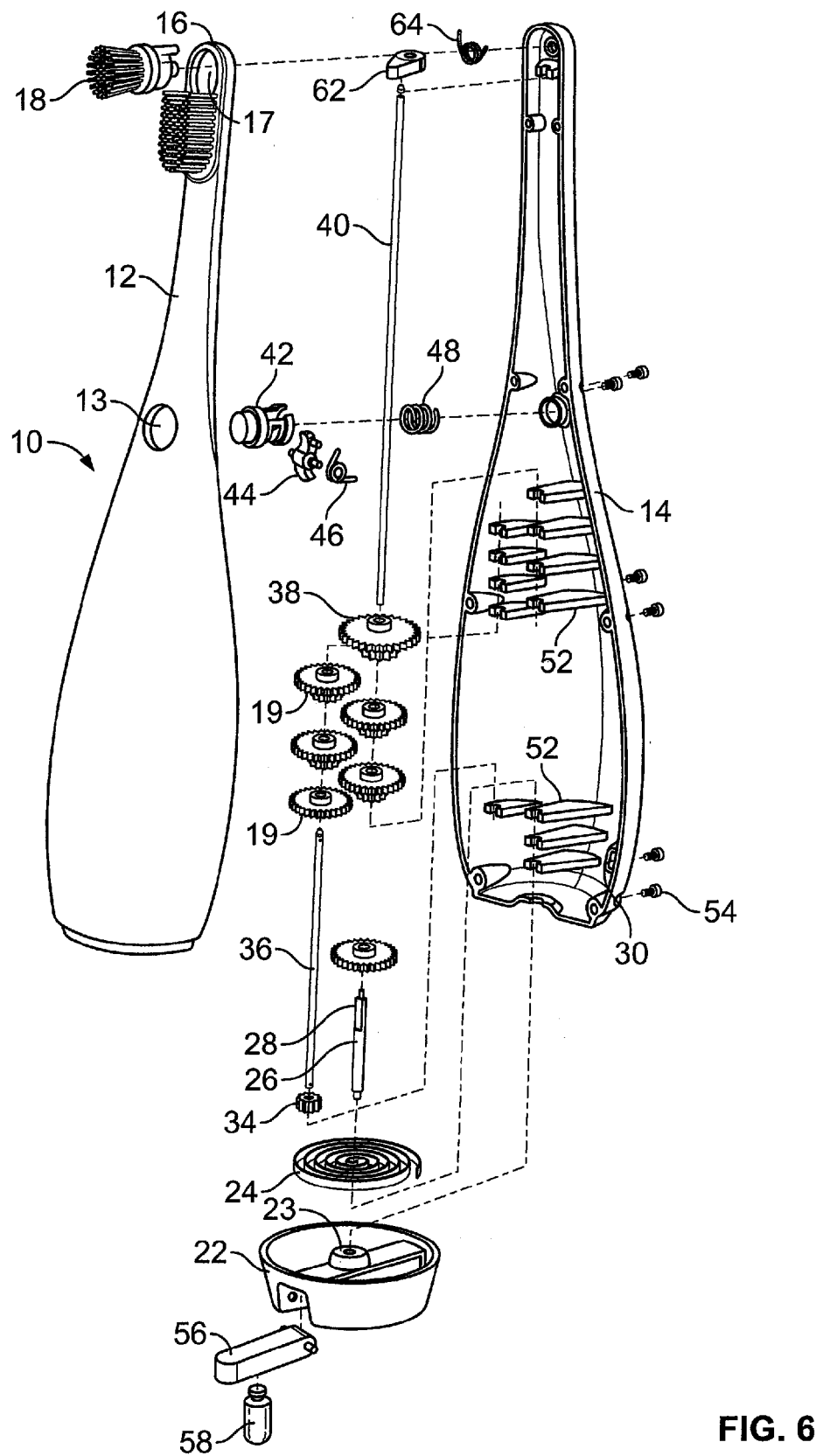
FIG. 6 is an exploded perspective view of the toothbrush of FIG. 5.
Figure 7:
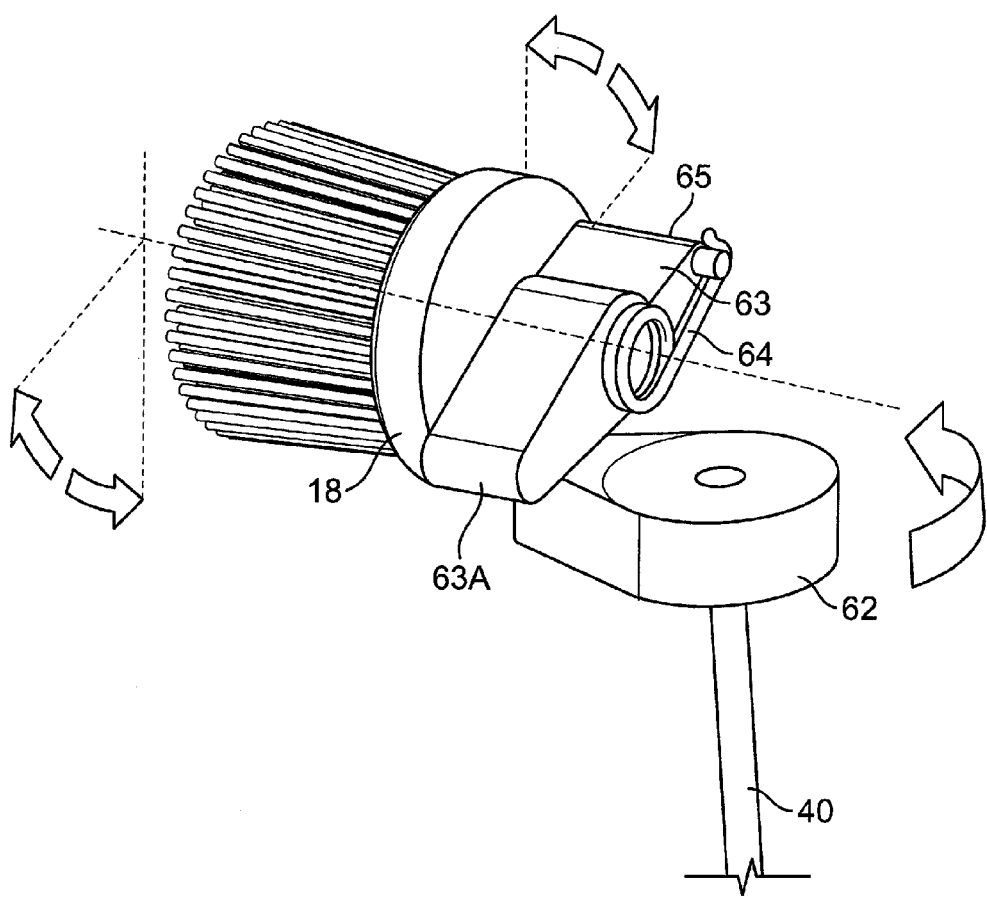
FIG. 7 is an enlarged view illustrating the mechanism that brings about the oscillation of the brush head.

The third embodiment illustrated in FIGS. 5-7 is similar to the first embodiment of FIGS. 1 and 2 in that it employs a movable brush head 18 movably fitted into the opening 17 at the upper end 16 of front valve housing 12. The action of brush head 18 of the third embodiment oscillates instead of rotating as it does in the embodiment of FIGS. 1 and 2. The spring wound power train of rotating the drive shaft 40 is identical to that used in the first two embodiments.

To accomplish the oscillation the drive shaft 40 has located at its end thereof the offset weight/cam 62 that is secured to and driven by the shaft 40. However, secured to the back of the brush 18 is a movably mounted lever 63 that is spring-biased downwardly by the spring 64 that is connected at one end of the rod 65 sticking out from the back of the brush head 18 and its other end in engagement with the lever 63. With this construction the brush head 18 is rotated counter-clockwise into position to be engaged by the rotating offset weight 62. When the weight/cam 62 engages the portion 63A of the lever 63 the weight moves the lever clockwise and after the weight/cam 62 becomes disengaged the lever 63 is moved counter-clockwise to again be engaged by the rotating weight 62 to bring about a high speed oscillating action of the brush head.

It can be seen from the above and the appended claims that there is illustrated three novel embodiments of a spring powered toothbrush in which the brush portions are rapidly moved to provide the desired cleaning action. The toothbrush is very compact and requires no exterior power source such as a battery or water pressure to obtain a fast moving brush cleaning action. The power is supplied by a wound-up spring that is easy to operate and has a long life.

It is intended to cover by the appended claims all modifications and embodiments which fall within the true spirit and scope of the invention.

What is claimed is:

1. A spring powered toothbrush for cleaning teeth comprising
    a toothbrush housing,
    a brush portion located at one end of the housing and having bristles on a side of the brush portion,
    a power operated drive mechanism for rapidly moving the brush portion, the power operated drive mechanism including a wind-up spring mechanism located at the other end of the housing,
    said brush portion including a fixed section and a movably mounted brush section and means for operably connecting said brush section to the drive mechanism to effect rapid movement of said brush section,
    and wherein said brush section is mounted for oscillating movement relative to the fixed section and includes a spring-biased lever arrangement movably mounted on a side of the brush section opposite said bristles and the power operated drive mechanism includes a drive shaft having an offset weight that periodically engages said lever to oscillate the brush section to aid in teeth cleaning; and
    control means for regulating the operation of the drive mechanism whereby when the control means is actuated the brush portion is rapidly moved to clean the teeth when the toothbrush is used.

2. A spring-powered toothbrush as set forth in claim 1 in which the power operated drive mechanism includes a rotatable cap secured to said other end of the housing, means for connecting the cap to a wind-up spring of said wind-up spring mechanism whereby the rotation of the cap will wind up the spring to provide the power for said drive mechanism.

3. A spring-powered toothbrush as set forth in claim 2 in which the wind-up spring has one end secured to said housing and the other end is secured to said rotatable cap.

4. A spring-powered toothbrush as set forth in claim 3 in which said cap defines a recess in its bottom surface and a lever and handle is pivotally connected to said cap for rotating same to load said spring and the handle can be disposed in said recess to place it in an out of the way location when the toothbrush is being used.

5. A spring-powered toothbrush as set forth in claim 3 in which the control means includes a button operated clutch means to control the operation of the power operated drive mechanism.

6. A spring-powered toothbrush as set forth in claim 3 in which the power operated drive mechanism includes a gear axle secured to said cap and having one end secured to said spring and a gear drive assembly connecting the gear axle to a drive shaft by which rapid movement of the brush portion is effected and the control means includes a button operated clutch mechanism for controlling the action between said gear drive assembly and drive shaft.

7. A spring-powered toothbrush as set forth in claim 1 including a spring secured at one end to the back of said brush section and at its other end to the lever to bias the lever into engagement with said offset weight to facilitate the oscillating movement of said brush section.

\* \* \* \* \*